(12) United States Patent
Omori

(10) Patent No.: US 8,696,554 B2
(45) Date of Patent: Apr. 15, 2014

(54) ENDOSCOPE AND MEDICAL SYSTEM

(75) Inventor: Koji Omori, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1143 days.

(21) Appl. No.: 12/266,891

(22) Filed: Nov. 7, 2008

(65) Prior Publication Data

US 2009/0216086 A1  Aug. 27, 2009

(30) Foreign Application Priority Data

Feb. 27, 2008  (JP) .................................. 2008-046647

(51) Int. Cl.
*A61B 1/06* (2006.01)
*A61B 1/00* (2006.01)
*A61B 1/04* (2006.01)

(52) U.S. Cl.
USPC ............................ 600/178; 600/132; 600/160

(58) Field of Classification Search
USPC .......................... 600/178, 132, 182, 160, 109
See application file for complete search history.

(56) References Cited

U.S. PATENT DOCUMENTS

| | | | | |
|---|---|---|---|---|
| 6,033,360 A | * | 3/2000 | Sano et al. ..................... | 600/178 |
| 6,409,391 B1 | * | 6/2002 | Chang ............................ | 385/53 |
| 6,969,348 B2 | * | 11/2005 | Araii .............................. | 600/178 |
| 6,997,868 B1 | * | 2/2006 | Uram ............................. | 600/133 |
| 7,001,331 B2 | * | 2/2006 | Kaji ............................... | 600/132 |
| 8,152,715 B2 | * | 4/2012 | Root et al. ..................... | 600/131 |
| 8,246,230 B2 | * | 8/2012 | Todd et al. .................... | 362/574 |
| 2005/0222499 A1 | * | 10/2005 | Banik et al. ................... | 600/132 |
| 2012/0002394 A1 | * | 1/2012 | Todd et al. ..................... | 362/13 |

FOREIGN PATENT DOCUMENTS

| | | |
|---|---|---|
| JP | S55-56603 | 4/1980 |
| JP | S56-34326 | 4/1981 |
| JP | 4-97312 | 3/1992 |
| JP | 4-125611 | 4/1992 |
| JP | 2006-102049 | 4/2006 |

* cited by examiner

*Primary Examiner* — Philip R Smith
*Assistant Examiner* — William Chou
(74) *Attorney, Agent, or Firm* — Scully, Scott, Murphy & Presser, P.C.

(57) ABSTRACT

An endoscope of the invention includes: an insertion portion including in a distal end portion thereof an image pickup portion for picking up an image of an object in a living body; an operation portion connected to a proximal end side of the insertion portion; a cable including a connector portion connectable to a processor for performing signal processing on a signal outputted when the image of the object is picked up; a light source portion for emitting light to illuminate the object, the light source portion being provided in the connector portion; a light transmitting portion for transmitting the light emitted from the light source portion to the distal end portion to emit the light to the object; and a heat-radiating portion capable of radiating heat emitted from the light source portion, the heat-radiating portion being provided in the connector portion.

2 Claims, 17 Drawing Sheets

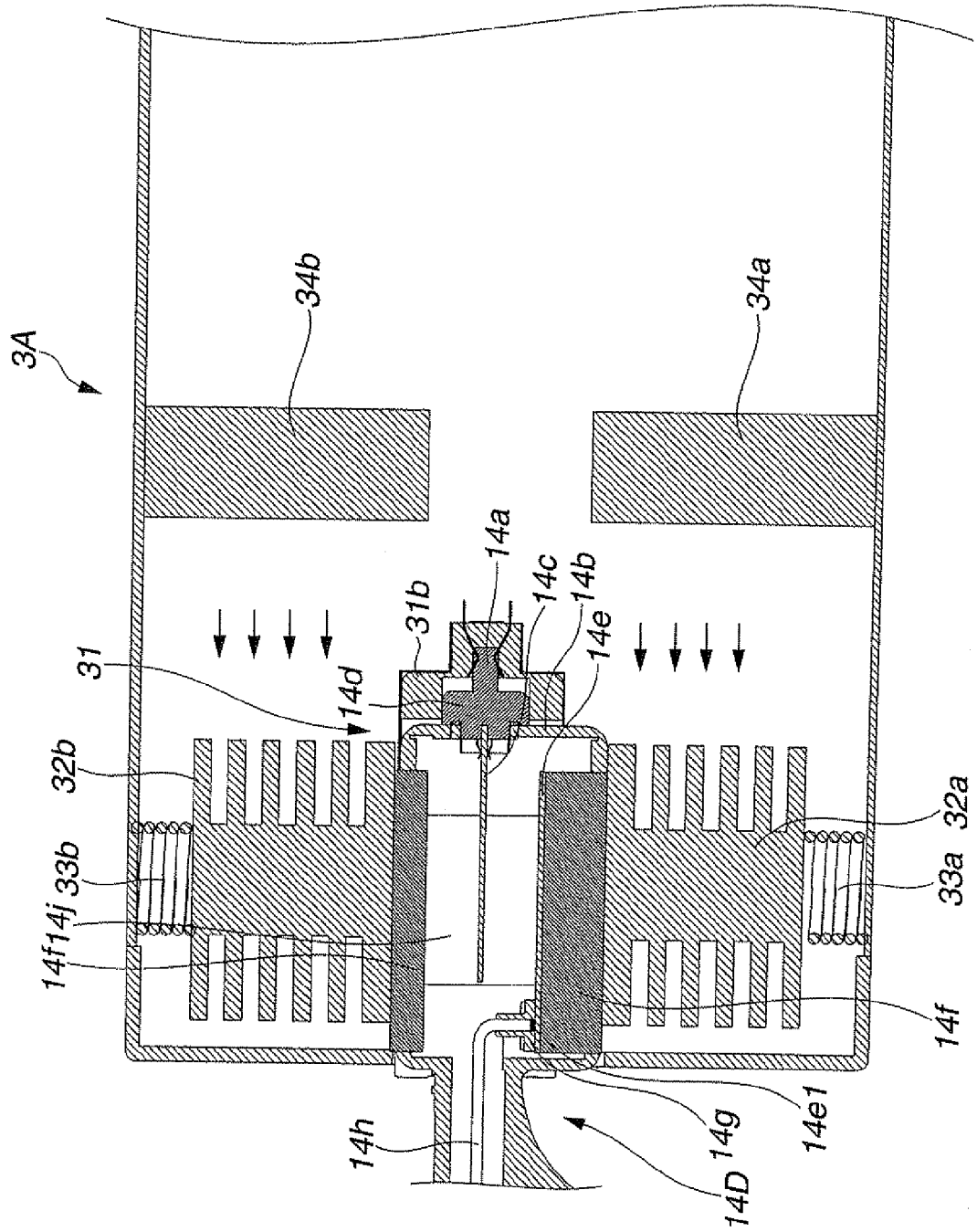

ENDOSCOPE AND MEDICAL SYSTEM

This application claims benefit of Japanese Application No. 2008-046647 filed on Feb. 27, 2008, the contents of which are incorporated by this reference.

BACKGROUND OF THE INVENTION

1. Field of the Invention

The present invention relates to an endoscope and a medical system, and more particularly to an endoscope and a medical system which include in a connector portion thereof a light source portion for emitting light to illuminate an object.

2. Description of Related Art

Conventionally, medical systems including an endoscope and a processor and the like to which the endoscope is connected have been primarily used for the application in which an operator and the like observe inside of a living body as a subject.

Furthermore, the endoscope is configured by including, for example, an insertion portion formed in a shape and size so as to be insertable into a living body, a distal end portion provided on a distal end side of the insertion portion, and an image pickup portion for picking up an image of an object in the living body, which is provided at the distal end portion.

Moreover, in recent years, Japanese Patent Application Laid-Open Publication No. 2006-102049, for example, proposes an endoscope provided at a distal end portion thereof with an LED (Light Emitting Diode) as a light source for emitting light to illuminate an object as an image pickup target of an image pickup portion.

SUMMARY OF THE INVENTION

An endoscope according to the present invention includes: an insertion portion having an elongated shape insertable into a living body and including in a distal end portion thereof an image pickup portion for picking up an image of an object in a living body; an operation portion connected to a proximal end side of the insertion portion; a cable whose one end side is extended from the operation portion, the cable including at the other end side thereof a connector portion connectable to a processor for performing signal processing on a signal outputted when the image of the object is picked up; a light source portion for emitting light to illuminate the object, the light source portion being provided in the connector portion; a light transmitting portion for transmitting the light emitted from the light source portion to the distal end portion to emit the light to the object; and a heat-radiating portion capable of radiating heat emitted from the light source portion, the heat-radiating portion being provided in the connector portion.

A medical system according to the present invention includes: an endoscope having a shape insertable into a living body and including an image pickup portion for picking up an image of an object in the living body; a processor for performing signal processing on a signal outputted when the image of the object is picked up; a cable whose one end side is extended from the endoscope, the cable including at the other end side thereof a connector portion connectable to the processor; a light source portion for emitting light to illuminate the object, the light source portion being provided in the connector portion; and a heat-radiating portion capable of radiating heat emitted from the light source portion, the heat-radiating portion being provided in the connector portion.

BRIEF DESCRIPTION OF THE DRAWINGS

FIG. 17 is a cross-sectional view showing a state inside of a processor having a configuration corresponding to the connector according to the modified example of the second embodiment, in a case where the connector is connected to the processor.

DETAILED DESCRIPTION OF PREFERRED EMBODIMENTS

Hereinafter, embodiments of the present invention will be described with reference to the drawings.

First Embodiment

Figure 1:
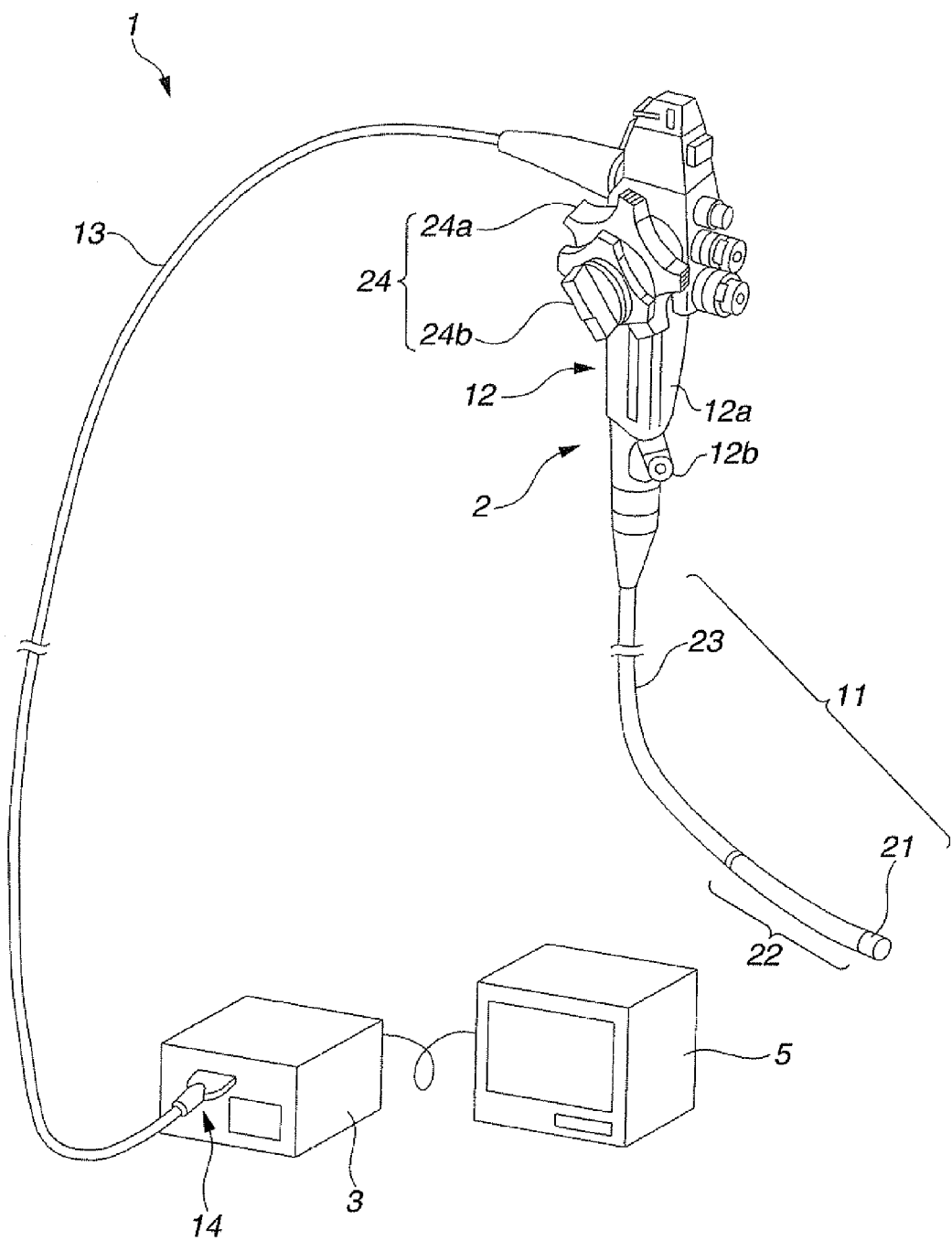
FIG. 1 is a view showing an exemplary configuration of an endoscope and an endoscope system as an example to which an embodiment of the present invention is applicable.
Figure 2:
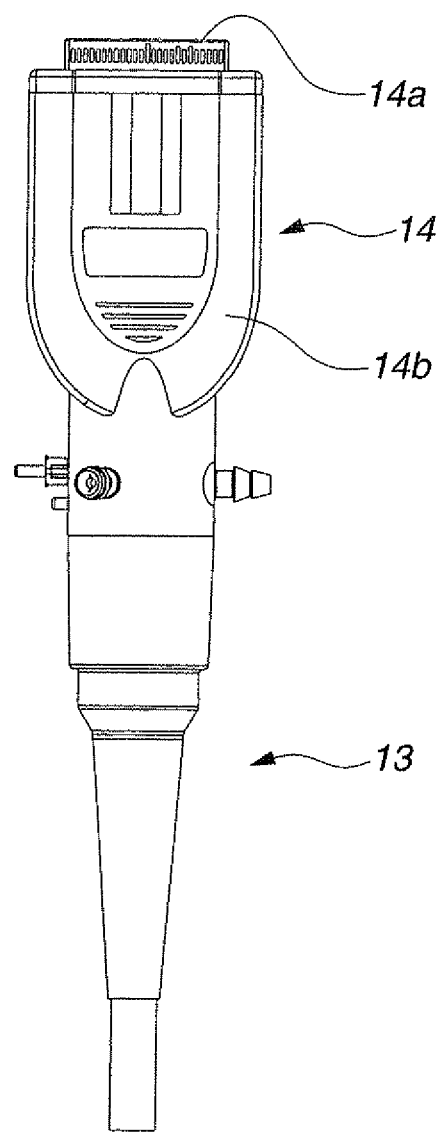
FIG. 2 is a view showing an appearance of a connector according to a first embodiment.
Figure 3:
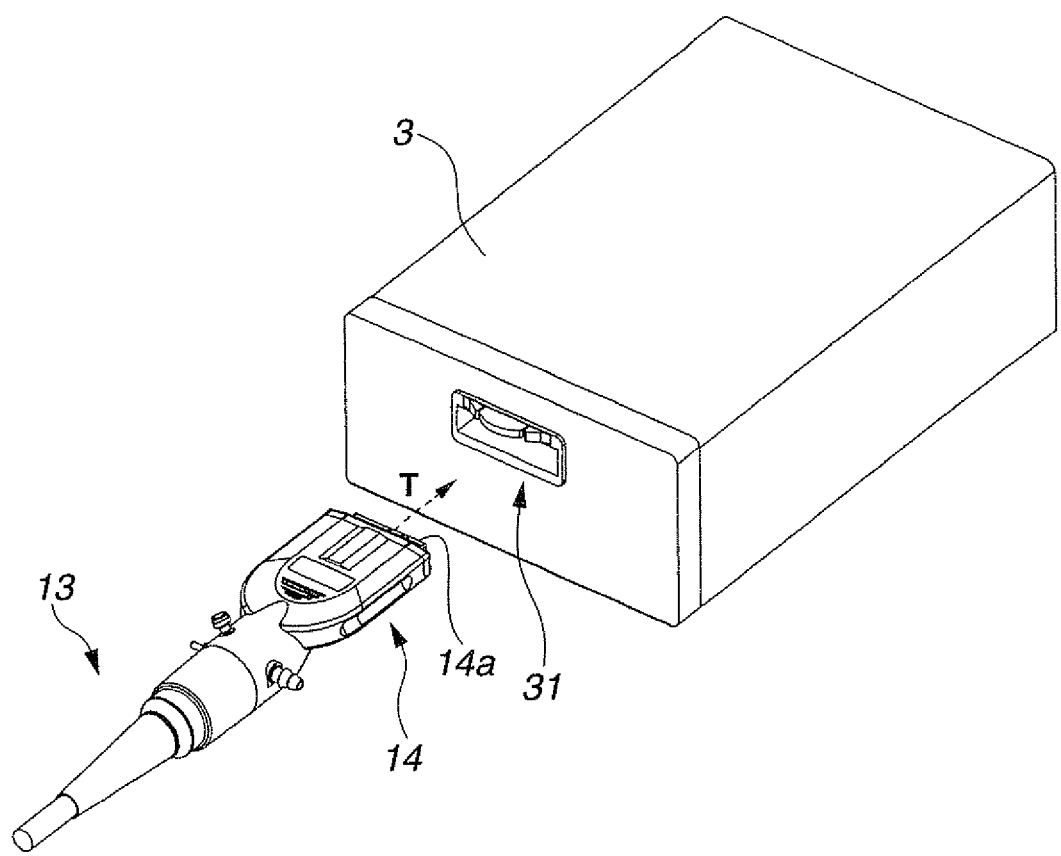
FIG. 3 is a view showing a state before the connector according to the first embodiment is plugged into a processor.
Figure 4:
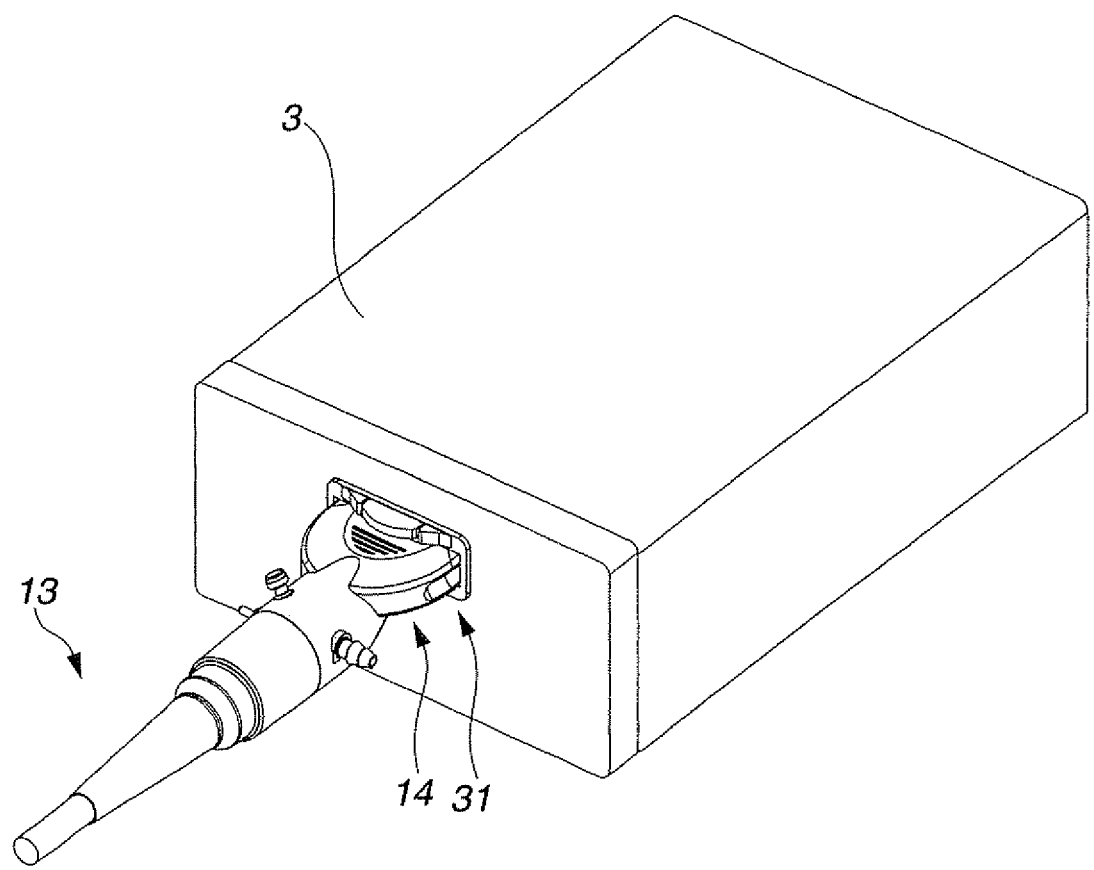
FIG. 4 is a view showing a state after the connector according to the first embodiment was plugged into the processor.
Figure 5:
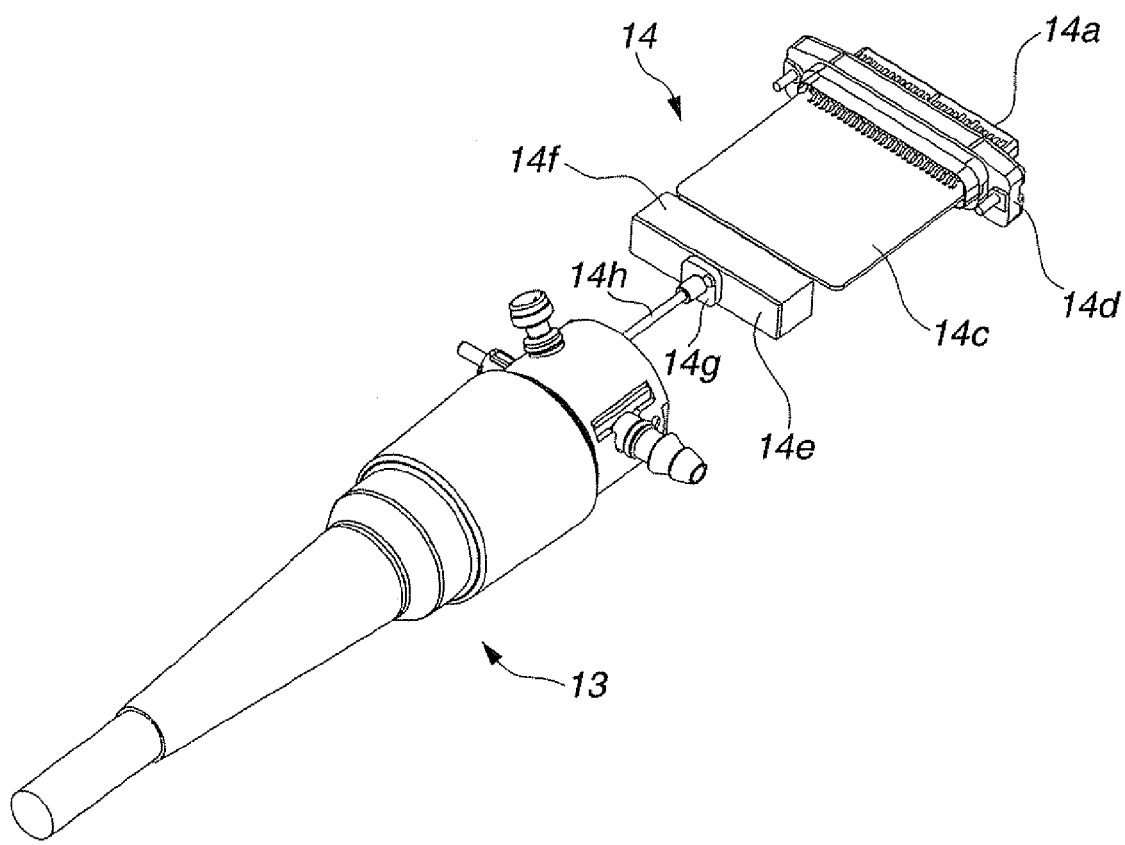
FIG. 5 is a view showing an example of an internal configuration of the connector according to the first embodiment.
Figure 6:
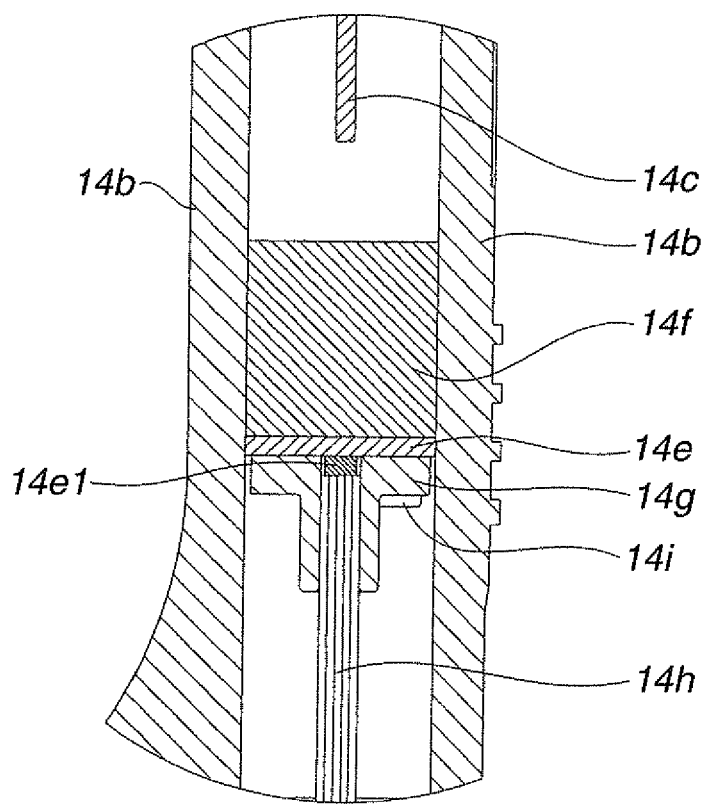
FIG. 6 is a partial cross-sectional view of the connector in FIG. 2 in a case where the connector is cut along a longitudinal central axis and seen from a side-surface side of the connector.
Figure 7:
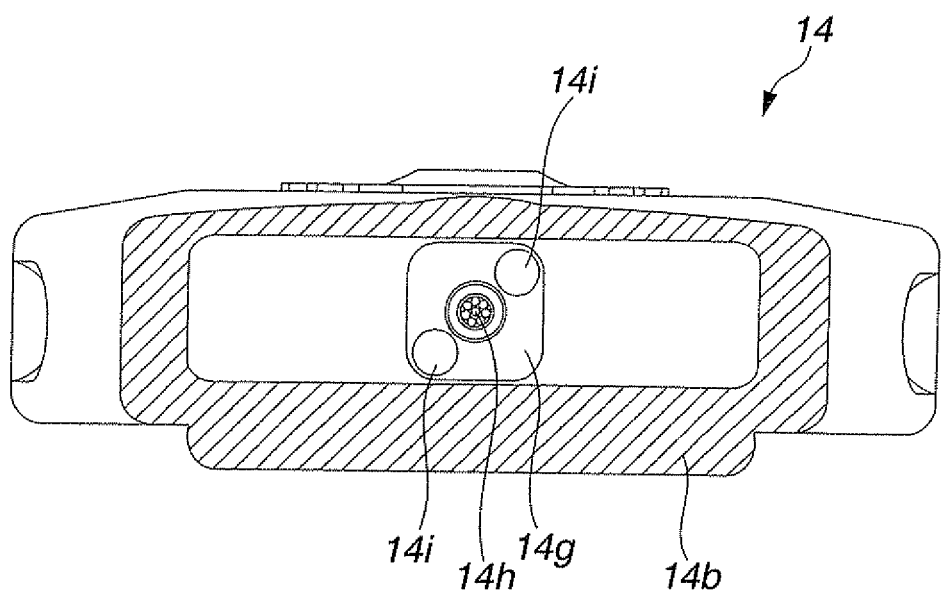
FIG. 7 is a cross-sectional view of the connector in FIG. 2 in a case where the connector is cut in a direction vertical to the central axis at a position where a fixing member is arranged and seen from a front face side of the connector.
Figure 8:
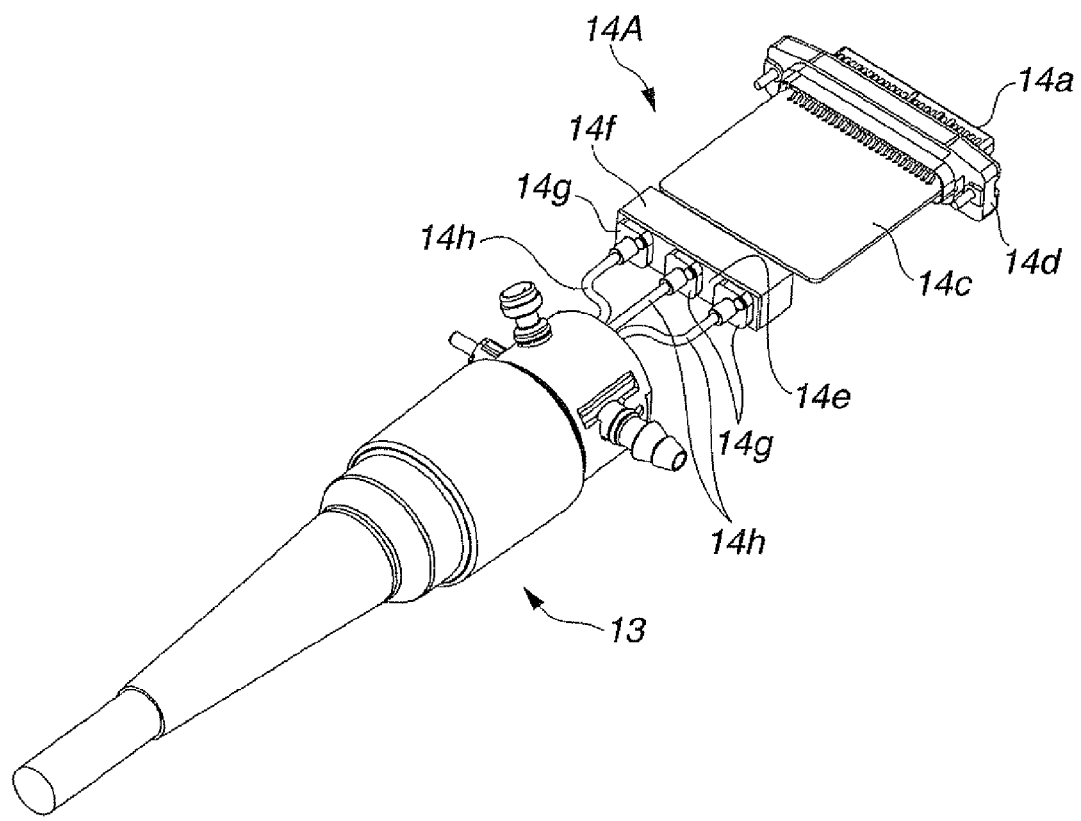
FIG. 8 is a view showing an example of an internal configuration of a connector according to a first modified example of the first embodiment.
Figure 9:
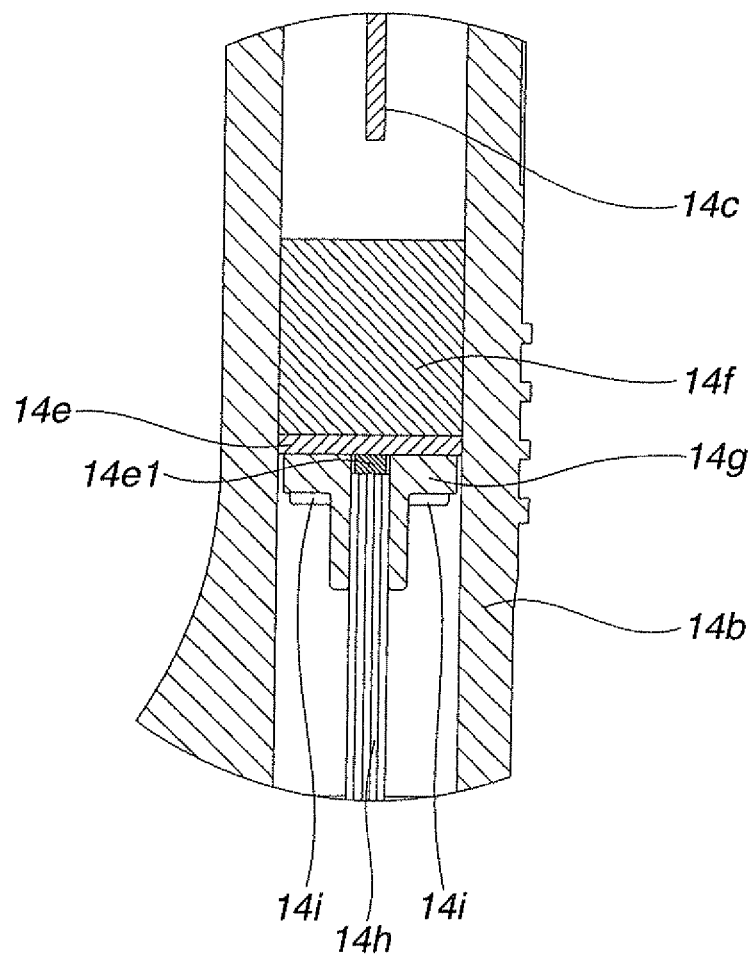
FIG. 9 is a partial cross-sectional view of the connector in FIG. 8 to which an exterior case is mounted, in a case where the connector is cut along the longitudinal central axis and seen from the side-surface side.
Figure 10:
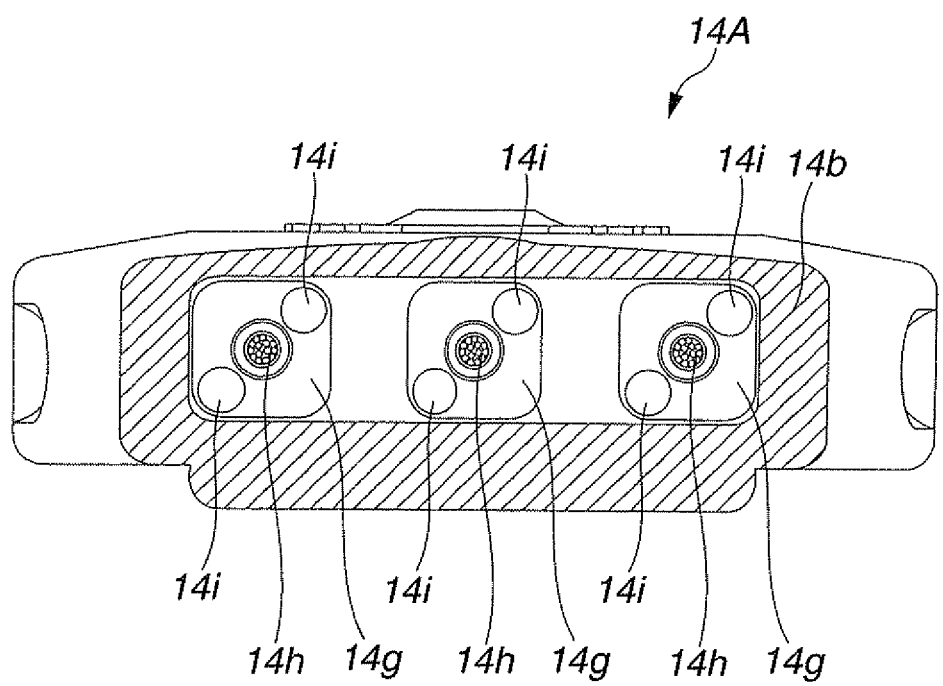
FIG. 10 is a cross-sectional view of the connector in FIG. 8 to which the exterior case is mounted, in a case where the connector is cut in the direction vertical to the central axis at the position where the fixing members are arranged and seen from the front face side.

FIGS. 1 to 13 relate to the first embodiment of the present invention. FIG. 1 is a view showing an exemplary configuration of an endoscope and an endoscope system as an example to which an embodiment of the present invention is applicable. FIG. 2 is a view showing an appearance of a connector according to the first embodiment. FIG. 3 is a view showing a state before the connector according to the first embodiment is plugged into a processor. FIG. 4 is a view showing a state after the connector according to the first embodiment was plugged into the processor. FIG. 5 is a view showing an example of an internal configuration of the connector according to the first embodiment. FIG. 6 is a partial cross-sectional view of the connector in FIG. 2 in a case where the connector is cut along a longitudinal central axis and seen from a side-surface side of the connector. FIG. 7 is a cross-sectional view of the connector in FIG. 2 in a case where the connector is cut in a direction vertical to the central axis at a position where fixing member is arranged and seen from a front face side of the connector. FIG. 8 is a view showing an example of an internal configuration of a connector according to a first modified example of the first embodiment. FIG. 9 is a partial cross-sectional view of the connector in FIG. 8 to which an exterior case is mounted, in a case where the connector is cut along the longitudinal central axis and seen from the side-surface side. FIG. 10 is a cross-sectional view of the connector in FIG. 8, to which the exterior case is mounted, in a case where the connector is cut in the direction vertical to the central axis at the position where the fixing members are arranged and seen from the front face side.

Figure 11:
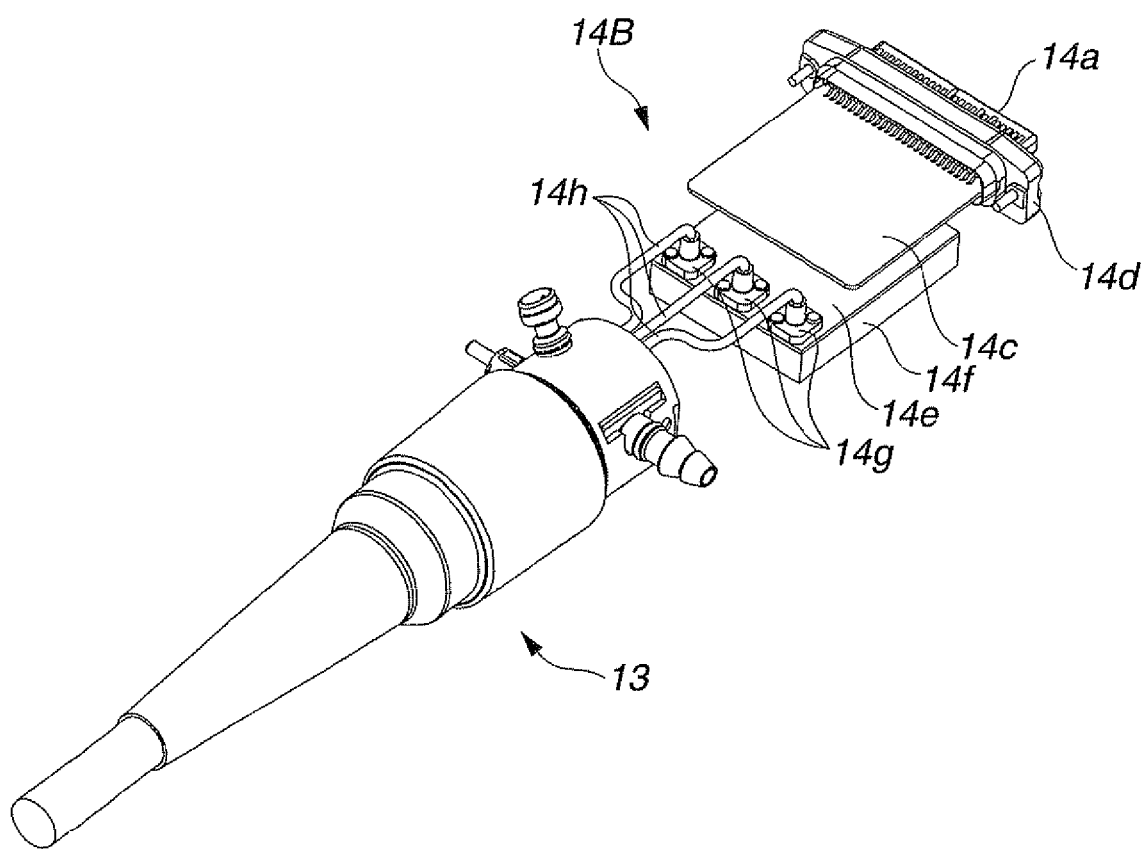
FIG. 11 is a view showing an example of an internal configuration of a connector according to a second modified example of the first embodiment.
Figure 12:
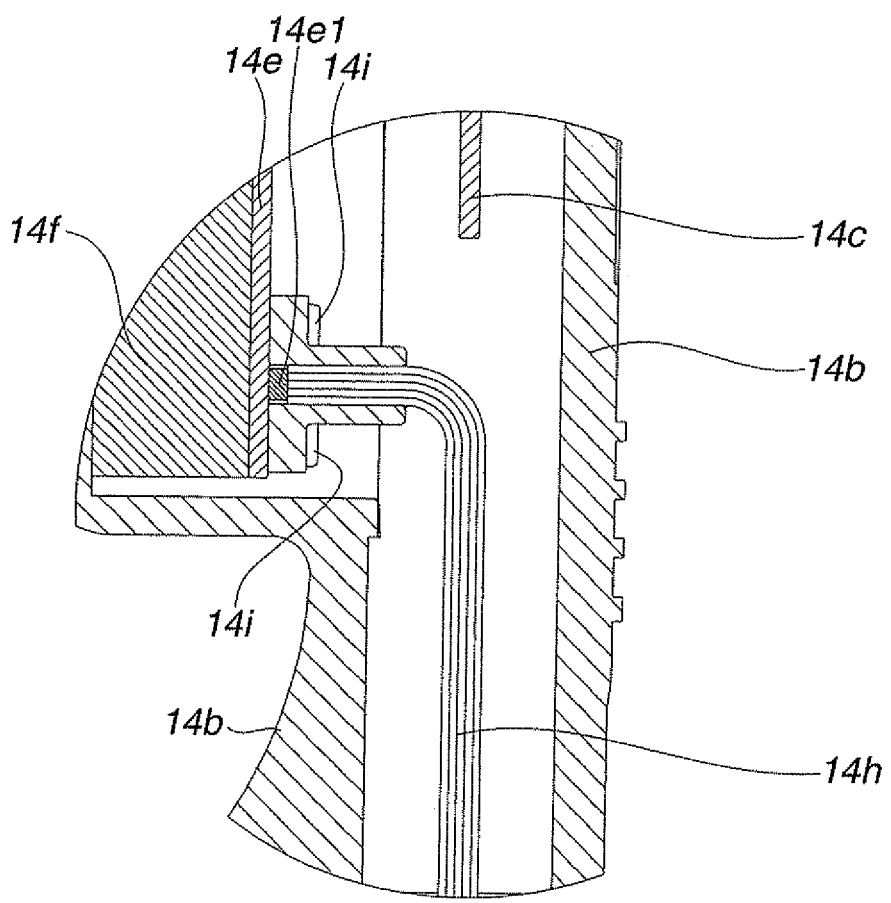
FIG. 12 is a partial cross-sectional view of the connector in FIG. 11 to which an exterior case is mounted, in a case where the connector is cut along the longitudinal central axis and seen from the side-surface side.
Figure 13:
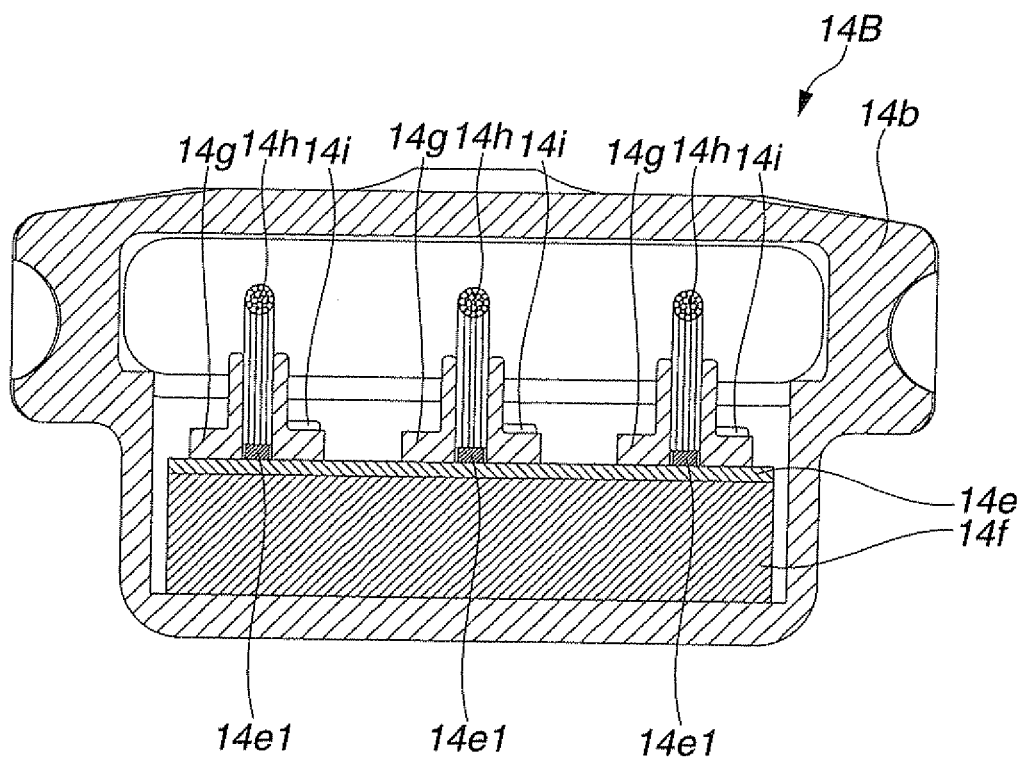
FIG. 13 is a cross-sectional view of the connector in FIG. 11 to which the exterior case is mounted, in a case where the connector is cut along the direction vertical to the central axis at the position where the fixing members are arranged and seen from the front face side.

FIG. 11 is a view showing an example of an internal configuration of a connector according to a second modified example of the first embodiment. FIG. 12 is a partial cross-sectional view of the connector in FIG. 11 to which an exterior case is mounted, in a case where the connector is cut along the longitudinal central axis and seen from the side-surface side. FIG. 13 is a cross-sectional view of the connector in FIG. 11 to which an exterior case is mounted, in a case where the connector is cut along the direction vertical to the central axis at the position where the fixing member are arranged and seen from the front face side.

As shown in FIG. 1, an endoscope system 1 as a medical system includes: an endoscope 2 which picks up an image of an object in a living body as a subject to output the picked-up image as an image pickup signal; a processor 3 connected to the endoscope 2, which applies a signal processing to the image pickup signal outputted from the endoscope 2 and outputs the processed signal while converting the signal into a video signal; and a monitor 5 which displays the image of the object based on the video signal outputted from the processor 3. The endoscope 2 includes: an insertion portion 11 having a shape and size insertable into a living body; an operation portion 12 including a grasping portion 12a, which is provided in a linked manner on a proximal end side of the insertion portion 11; a universal cable 13 one end side of which is extended from a side surface of the operation portion 12; and a connector 14 which is provided at an end portion on the other end side of the universal cable 13 and detachably connected to the processor 3.

The insertion portion 11 includes in a linked manner: a distal end portion 21 provided on a distal end side; a bendable bending portion 22 provided at a rear portion of the distal end portion 21; and an elongated flexible tube portion 23 provided at a rear portion of the bending portion 22. Note that the distal end portion 21 is assumed to be provided with an image pickup portion including an objective optical system, not shown, for forming an image of an object and an image pickup device, not shown, for picking up the image of the object formed by the objective optical system and outputting the image as an image pickup signal.

The operation portion 12 is provided with, for example, a bending operation portion 24 including a bending operation knob 24a for bending and operating the bending portion 22 and a fixing lever 24b for fixing the bending operation knob 24a at a desired rotational position. Furthermore, the operation portion 12 is provided with a treatment instrument insertion port 12b communicating with a proximal end side of a treatment instrument channel, not shown, as a conduit provided through the insertion portion 11.

The connector 14, which is provided at the end portion of the universal cable 13, includes on a distal end side thereof a terminal portion 14a, as shown in FIG. 2, for example. The connector 14 is pushed into the processor 3 in a direction indicated by a dashed arrow T from the state as shown in FIG. 3, for example, that is, the state in which the surface on the side where the terminal portion 14a is provided is made to face a connector receiving portion 31 provided to the processor 3. Thereby, the connector 14 is connected to the processor 3, as in the state shown in FIG. 4. In this state, the terminal portion 14a contacts a plurality of terminals, not shown, provided in the connector receiving portion 31, and thereby the endoscope 2 and the processor 3 are electrically connected to each other.

In addition, as shown in FIG. 2, for example, parts of the connector 14 other than the terminal portion 14a are covered with an exterior case 14b.

As shown in FIG. 5, the connector 14 further includes: a signal substrate 14c for inputting and outputting various signals; a contact unit 14d for electrically connecting between the terminal portion 14a and the signal substrate 14c; an LED substrate 14e having a function as a light source portion; a heat-radiating member 14f; a fixing member 14g; and a light guide bundle 14h.

As shown in FIG. 6, the LED substrate 14e formed of for example an aluminum substrate includes on a surface on one side thereof an LED 14e1 which is turned on or off in response to an LED driving signal inputted through the signal substrate 14c. The surface on the other side of the LED substrate 14e contacts substantially entirely the heat-radiating member 14f.

That is, the light source portion according to the present embodiment is configured of the LED substrate 14e and the LED 14e1.

On the other hand, for example as shown in FIGS. 6 and 7, the LED 14e1 and the light guide bundle 14h are positioned inside of the exterior case 14b at a position where a light incident end surface of the light guide bundle 14h contacts a light emitting surface of the LED 14e1, and fixed at the position after the positioning by a fixing member 14g and a screw member 14i.

The light guide bundle 14h having a function as a light transmitting portion is configured by binding a plurality of elongated light transmitting members such as optical fibers. In addition, the light guide bundle 14h has the light incident end surface arranged at a position contacting the light emitting surface of the LED 14e1. The light guide bundle 14h is inserted through the universal cable 13, the operation portion 12, and the insertion portion 11, and has the light emitting end surface arranged in the vicinity of an illumination window, not shown, of the distal end portion 21. According to this configuration, the light emitted from the light emitting surface of the LED 14e1 is transmitted by the light guide bundle 14h, and thereafter emitted to the object as the image pickup target of the image pickup portion via the illumination window, not shown, provided at the distal end portion 21, for example.

Here working of the present embodiment will be described.

First, the operator connects each of the portions in the endoscope system 1 to activate each of the portions. This allows an LED driving signal to be outputted from the processor 3.

The LED substrate 14e drives the LED 14e1 based on the LED driving signal inputted when the processor 3 is activated, and emits heat as the LED 14e1 is driven. The heat emitted from the LED substrate 14e is transferred immediately to the heat-radiating member 14f and radiated inside of the exterior case 14b.

Since the connector 14 has the above-described configuration and working, heat hardly remains in the LED substrate 14e. As a result, in the endoscope 2 including the connector 14 according to the present embodiment, even in a case of long hours of observation for example, decrease in light amount due to the heat from the LED 14e1 hardly occurs, and it is possible to continuously illuminate the object with light amount suitable for observation.

In addition, as described above, in the present embodiment, the LED substrate 14e and the LED 14e1 are provided in the connector 14 which does not easily contact directly inside the living body as a subject. As a result, the endoscope 2 having the connector 14 according to the present embodiment eliminates the need to consider heat conduction into the living body as a subject. Therefore, compared with the configuration in which the LED substrate 14e and the LED 14e1 are provided in the distal end portion 21, for example, it is possible to illuminate the object in the living body with a larger amount of light.

Note that the connector 14 according to the present embodiment is not limited to the one including only one LED 14e1 on the LED substrate 14e, but may be configured as a connector 14A including three LEDs 14e1 on the LED substrate 14e, as shown in FIG. 8, for example.

In this case, the connector 14A includes three fixing members 14g and three light guide bundles 14h, which correspond to the three LEDs 14e1.

For example, as shown in FIGS. 9 and 10, the LEDs 14e1 and the light guide bundles 14h are respectively positioned such that the light emitting surface and the light incident end surface are in the above-described positional relationship, and thereafter fixed at the positions after the positioning by the fixing members 14g and the screw members 14i.

Note that the working of the connector 14A is the same as that of the connector 14 except for parts related to the number of the LEDs 14e1. Therefore, the description thereof will be omitted hereafter.

According to the above-described configuration, also in a case where the connector 14A as a first modified example of the present embodiment is provided in the endoscope 2, it is possible to obtain the same effects as those in the case where the connector 14 is provided in the endoscope 2.

In addition, the connector 14A is not limited to one in which a substrate surface of the LED substrate 14e and the light emitting surfaces of the LEDs 14e1 are provided vertically with respect to a substrate surface of the signal substrate 14c. As shown in FIG. 11, for example, the connector 14A may be configured as a connector 14B in which the substrate surface of the LED substrate 14e and the light emitting surfaces of the LEDs 14e1 are provided horizontally with respect to the substrate surface of the signal substrate 14c.

In this case, the light guide bundles 14h are arranged inside of the exterior case 14b such that end portions on the light incident end surface side are bent in a vertical direction with respect to the substrate surface of the signal substrate 14c.

As shown in FIGS. 12, 13, for example, the LEDs 14e1 and the end portions of the light guide bundles 14h are respectively positioned such that the light emitting surface and the light incident end surface are in the above-described positional relationship, and thereafter fixed at the positions after the positioning by the fixing members 14g and the screw members 14i.

Note that the working of the connector 14B is substantially the same as that of the connector 14A. Therefore, the description thereof will be omitted hereafter.

According to the above-described configuration, in the connector 14B as a second modified example of the present embodiment, the area of the substrate surface of the LED substrate 14e can be made larger compared with the case of the connector 14A. Therefore, a larger number of LEDs 14e1 can be provided on the LED substrate 14e in the case where the connector 14B is provided in the endoscope 2, compared with the case where the connector 14A is provided in the endoscope 2.

Furthermore, according to the above-described configuration, in the connector 14B as the second modified example of the present embodiment, the area of the heat-radiating member 14f can be made larger compared with the case of the connector 14A. Therefore, in the case where the connector 14B is provided in the endoscope 2, a more remarkable effect can be obtained in that heat hardly remains in the LED substrate 14e, compared with the case where the connector 14A is provided in the endoscope 2.

Note that the LEDs 14e1 included in the connector 14A and the connector 14B may all emit lights having the same wavelength band, or may each emit light having a different wavelength band. Alternatively only one of the LEDs 14e1 may emit light having a different wavelength band.

Second Embodiment

Figure 14:
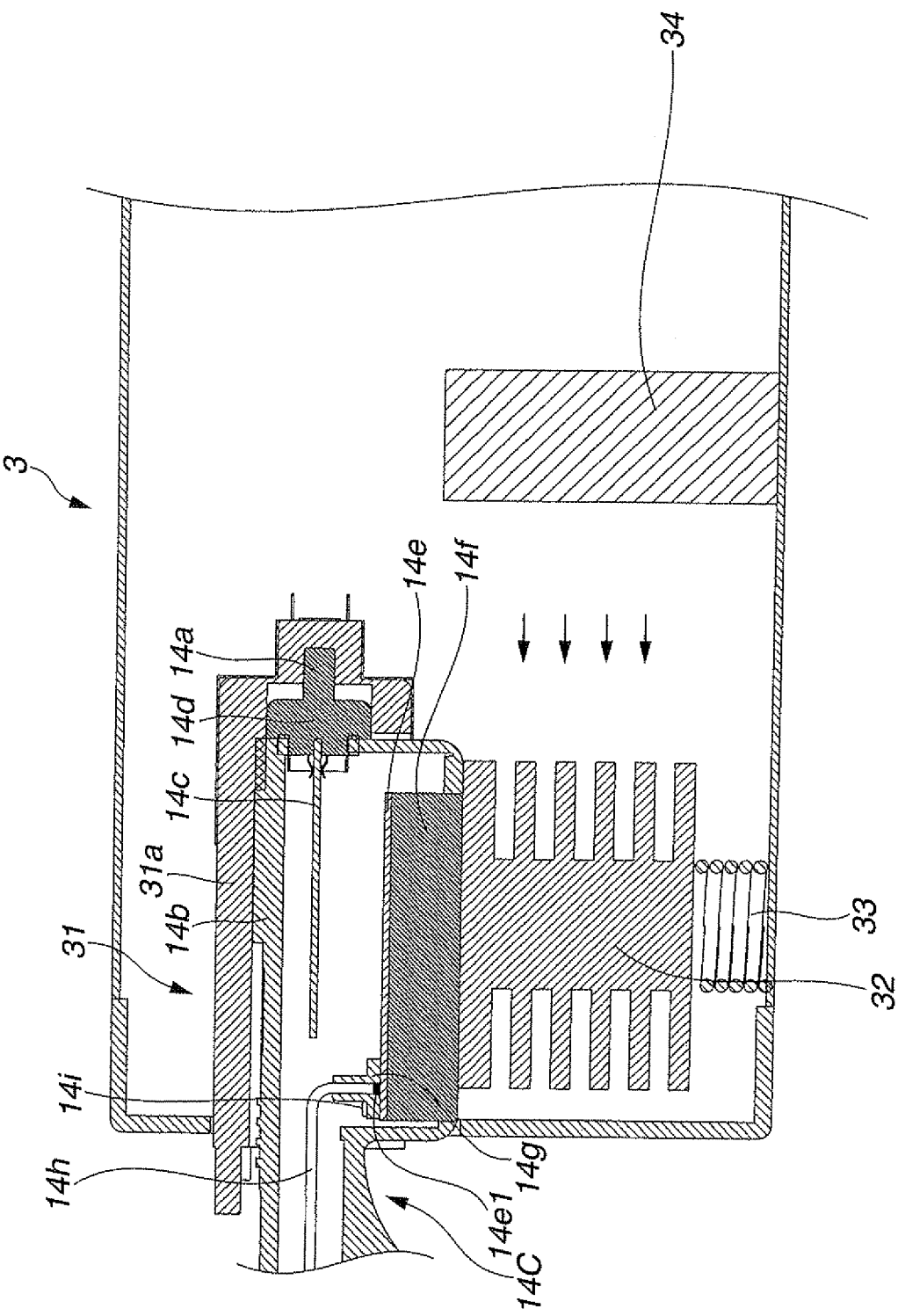
FIG. 14 is a cross-sectional view showing a state inside of a processor having a configuration corresponding to a connector according to the second embodiment, in a case where the connector is connected to the processor.
Figure 15:
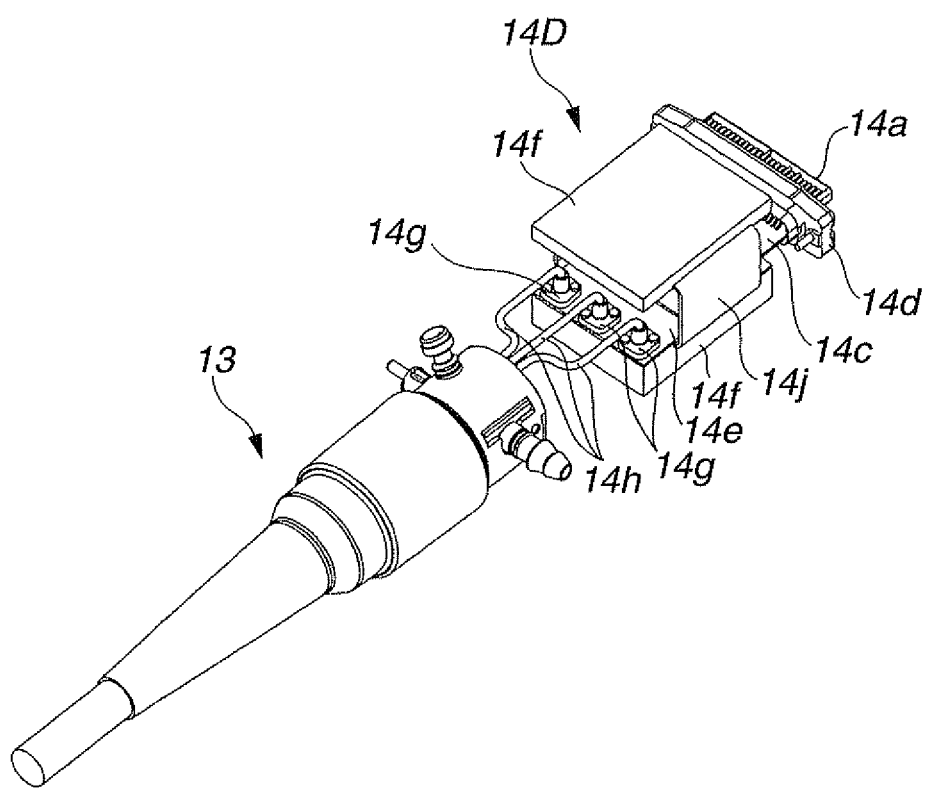
FIG. 15 is a view showing an example of an internal configuration of a connector according to a modified example of the second embodiment.
Figure 16:
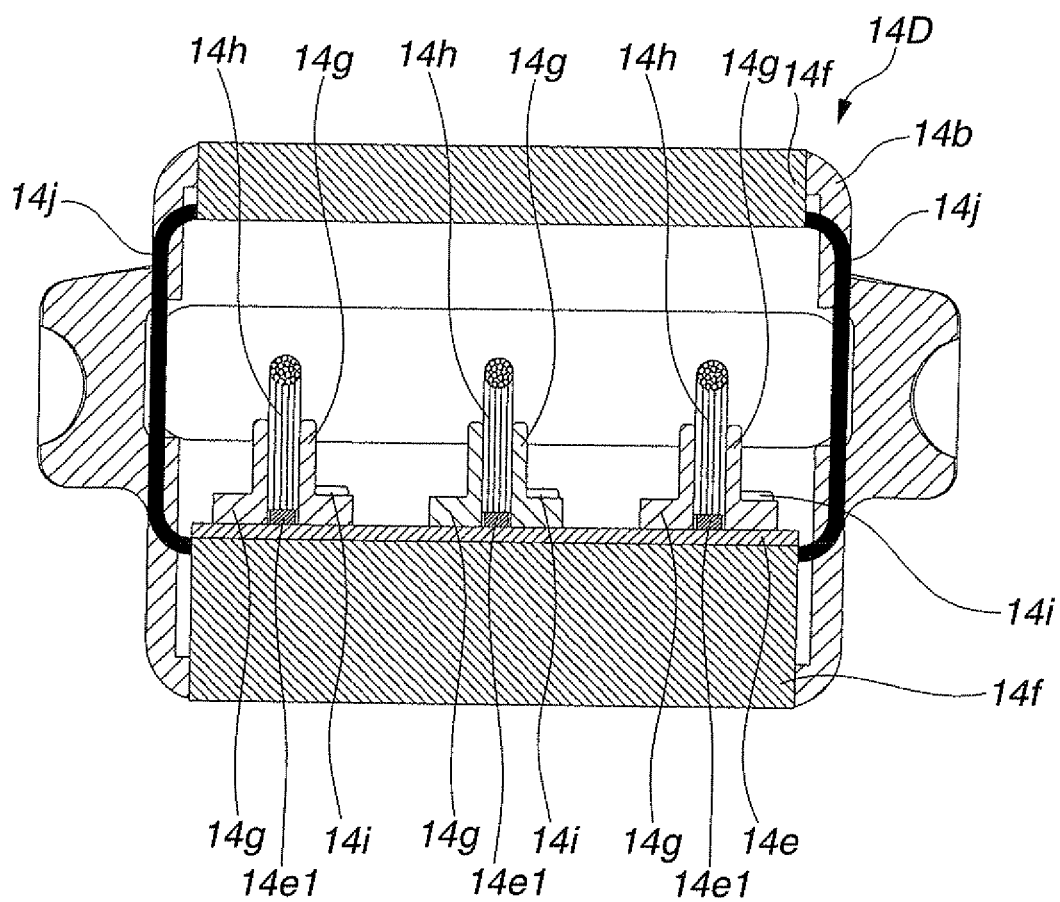
FIG. 16 is a cross-sectional view of the connector in FIG. 15 to which an exterior case is mounted, in a case where the connector is cut in the direction vertical to the central axis at the position where the fixing members are arranged and seen from the front face side.

FIGS. 14 to 17 relate to the second embodiment of the present invention. FIG. 14 is a cross-sectional view showing a state inside of a processor having a configuration corresponding to a connector according to the second embodiment, in a case where the connector is connected to the processor FIG. 15 is a view showing an example of an internal configuration of a connector according to a modified example of the second embodiment. FIG. 16 is a cross-sectional view of the connector in FIG. 15 to which an exterior case is mounted, in a case where the connector is cut in the direction vertical to the central axis at the position where the fixing member is arranged and seen from the front face side. FIG. 17 is a cross-sectional view showing a state inside of a processor having a configuration corresponding to a connector according to a modified example of the second embodiment, in a case where the connector is connected to the processor.

Note that in the following description, detailed descriptions on the parts having the same configurations as those in the first embodiment will be omitted. In addition, the configurations of the portions in the present embodiment are similar to those of the portions in the first embodiment. Therefore, in the present embodiment, description will be mainly made on the portions different from those in the first embodiment.

In the present embodiment, heat emitted from the LED substrate can be radiated in a state where the connector is connected to the processor.

Specifically, as shown in FIG. 14, a connector 14C according to the present embodiment has a configuration in which a part of the heat-radiating member 14f provided in the connector 14B of the first embodiment is exposed from the exterior case 14b.

Note that, among the portions of the connector 14C, the portions other than the above-described one have the same configurations as those in the connector 14B described already in the first embodiment. Therefore, detailed descriptions thereof will be omitted hereafter.

On the other hand, the processor 3 according to the present embodiment includes inside thereof: a receptacle 31a having a shape fittable to the connector 14C which is plugged into the connector receiving portion 31; a heat-radiating member 32; a flexible member 33; and a fan 34, as shown in FIG. 14.

The heat-radiating member 32 as a heat-receiving portion, which includes a heatsink formed of a material having high heat radiation such as aluminum, is arranged inside of the processor 3 at a position contacting an exposed surface of the heat-radiating member 14f when the connector 14C is connected (fitted) to the receptacle 31a.

Note that the heat-radiating member 32 is not limited to one configured by including the heatsink, as long as the heat-radiating member 32 has a configuration capable of radiating the heat emitted from the heat-radiating member 14f. For example, the heat-radiating member 32 may be configured by including a heat-radiating sheet, heat pipe, or the like.

The flexible member 33 formed of a spring member and the like, for example, is connected to the heat-radiating member 32, and provided for example at a position in the processor 3, shown in FIG. 14 as a position where the contacting state between the exposed surface of the heat-radiating member 14f and the heat-radiating member 32 when the connector 14C is plugged into the connector receiving portion 31 can be maintained.

The fan 34 as a heat-diffusing portion is arranged in the processor 3 at a position where the fan can send air to the heat-radiating member 32.

That is, a cooling portion in the processor 3 according to the present embodiment includes the heat-radiating member 32 and the fan 34.

Note that the processor 3 according to the present embodiment is not limited to one configured by including the fan 34 as long as the processor 3 has a configuration capable of removing the heat transferred to the heat-radiating member 32. The processor 3 may be configured by including a heat pipe, a graphite sheet, or the like, for example. In addition, the heat-diffusing portion included in the processor 3 according to the present embodiment is not limited to one formed of the fan 34 as long as the heat-diffusing portion can diffuse the heat transferred to the heat-radiating member 32. The heat-diffusing portion may be configured of means such as natural convection from a ventilation port or water cooling, for example.

Here, a working of the present embodiment will be described.

When the connector 14C is connected to (plugged into) the connector receiving portion 31, the connector 14C is fitted to the receptacle 31 and the exposed surface of the heat-radiating member 14f contacts the heat-radiating member 32.

On the other hand, the LED substrate 14e drives the LEDs 14e1 based on the LED driving signal inputted when the processor 3 is activated, and emits heat when the LEDs 14e1 is driven.

The heat emitted from the LED substrate 14e is transferred to the heat-radiating member 32 through the heat-radiating member 14f. Then the heat transferred to the heat-radiating member 32 is diffused in the processor 3 by sending air from the fan 34.

According to the above-described configurations and workings of the processor 3 and the connector 14C, heat hardly remains in the LED substrate 14e. As a result, in the endoscope system 1 including the processor 3 and the connector 14C according to the present embodiment, even in a case of long hours of observation for example, decrease in light amount due to the heat from the LED 14e1 hardly occurs, and it is possible to continuously illuminate the object with light amount suitable for observation.

Furthermore, as described above, the LED substrate 14e and the LEDs 14e1 are provided in the connector 14C which does not easily contact directly inside the living body as a subject in the present embodiment. As a result, the endoscope 2 having the connector 14C according to the present embodiment eliminates the need to consider heat conduction into the living body as a subject. Therefore, compared with the configuration in which the LED substrate 14e and the LEDs 14e1 are provided in the distal end portion 21, for example, it is possible to illuminate the object in the living body with a larger amount of light.

Furthermore, according to the configuration of the connector 14C of the present embodiment, almost the same effects as those of the connector 14B as the second modified example of the first embodiment can also be obtained.

Note that the connector 14C of the present embodiment is not limited to one in which the heat-radiating member 14f is provided at one location on the lower surface side. The connector 14C may be configured as a connector 14D in which the heat-radiating members 14f are provided at two locations, as shown in FIGS. 15 and 16, for example. Note that, in this case, the processor 3 of the present embodiment is configured as a processor 3A as shown in FIG. 17, for example, which has a configuration corresponding to the connector 14D.

As shown in FIGS. 15 and 16, for example, the connector 14D has at two locations, that is, on the upper surface side and the lower surface side, the heat-radiating members 14f a part of which is exposed from the exterior case 14b, and the heat-radiating members 14f are connected to each other by a heat-transfer member 14j.

Note that the heat-radiating member 14f on the upper surface side of the connector 14D is assumed to be provided inside of the connector 14D at a position sufficiently distant from the signal substrate 14c.

In addition, among the portions of the connector 14D, the portions other than the above-described ones have the same configuration as those in the connector 14C. Therefore, detailed descriptions thereof will be omitted hereafter.

On the other hand, as shown in FIG. 17, the processor 3A having the configuration corresponding to the connector 14D includes inside thereof: a receptacle 31b having a shape fittable to the connector 14D connected (plugged) to the connector receiving portion 31b; heat-radiating members 32a, 32b; flexible members 33a, 33b; and fans 34a, 34b.

The heat-radiating member 32a as a heat-receiving portion, which includes a heatsink formed of a material having high heat radiation such as aluminum, is arranged inside of the processor 3A at a position contacting an exposed surface of the heat-radiating member 14f on the lower surface side of the connector 14D when the connector 14D is connected (fitted) to the receptacle 31b. In addition, the heat-radiating member 32b as a heat-receiving portion, which includes a heatsink formed of a material having high heat radiation such as aluminum, is arranged inside of the processor 3A at a position contacting an exposed surface of the heat-radiating member 14f on the upper surface side of the connector 14D when the connector 14D is connected (fitted) to the receptacle 31b.

Note that the configuration of the heat-radiating members 32a, 32b are not limited to one configured by including the heatsink, as long as the heat-radiating members 32a, 32b can radiate the heat emitted from the heat-radiating member 14f on the upper surface side and the heat-radiating member 14f on the lower surface side, respectively. The heat-radiating members 32a, 32b may be configured by including a heat-radiating sheet or a heat pipe, for example.

The flexible member 33a formed of a spring member and the like, for example, is connected to the heat-radiating member 32a, and provided for example at a position in the processor 3A, shown in FIG. 17 as the position where the contacting state between the exposed surface of the heat-radiating member 14f on the lower surface side of the connector 14D and the heat-radiating member 32a when the connector 14D plugged into the connector receiving portion 31 can be maintained. The flexible member 33b formed of a spring member and the like, for example, is connected to the heat-radiating member 32b, and provided for example at a position in the processor 3A, shown in FIG. 17, as the position where the contacting state between the exposed surface of the heat-radiating member 14f on the upper surface side of the connector 14D and the heat-radiating member 32b when the connector 14D is plugged into the connector receiving portion 31 can be maintained.

The fan 34a is arranged in the processor 3A at a position where the fan can send air to the heat-radiating member 32a. Furthermore, the fan 34b is arranged in the processor 3A at a position where the fan can send air to the heat-radiating member 32b.

That is, a cooling portion in the processor 3A according to the present embodiment includes the heat-radiating members 32a, 32b and the fans 34a, 34b.

Note that the processor 3A as a modified example of the present embodiment is not limited to one configured by including the fans 34a, 34b, as long as the processor 3A has a configuration capable of removing the heat transferred to the heat-radiating members 32a, 32b. The processor 3A may be configured by including a heat pipe, a graphite sheet, or the like, for example. In addition, the heat-diffusing portion included in the processor 3A according to the modified example of the present embodiment is not limited to one formed of the fans 34a, 34b as long as the heat-diffusing portion can diffuse the heat transferred to the heat-radiating members 32a, 32b. The heat-diffusing portion may be configured of means such as natural convection from a ventilation port or water cooling, for example.

According to such a configuration, the heat emitted from the LED substrate 14e is transferred to the heat-radiating member 32a through the heat-radiating member 14f on the lower surface side of the connector 14D, and also transferred to the heat-radiating member 32b through the heat-transfer member 14j and the heat-radiating member 14f on the upper surface side of the connector 14D.

Then the heat transferred to the heat-radiating members 32a, 32b are diffused inside of the processor 3A by sending air from the fans 34a, 34b.

As described above, the configuration by the processor 3A and the connector 14D as a modified example of the present embodiment makes heat more difficult to remain in the LED substrate 14e than in the configuration by the processor 3 and the connector 14C. As a result, in the endoscope system 1 including the processor 3A and the connector 14D as a modified example of the present embodiment, even in a case of long hours of observation for example, decrease in light amount due to the heat from the LEDs 14e1 hardly occurs, and it is possible to continuously illuminate the object with light amount suitable for observation.

In addition, as described above, in the present embodiment, the LED substrate 14e and the LEDs 14e1 are provided in the connector 14D which does not easily contact directly inside the living body as a subject. As a result, the endoscope 2 having the connector 14D according to the present embodiment eliminates the need to consider heat conduction into the living body as a subject. Therefore, compared with the configuration in which the LED substrate 14e and the LEDs 14e1 are provided in the distal end portion 21, for example, it is possible to illuminate the object in the living body with a larger amount of light.

Furthermore, according to the configuration of the connector 14D as a modified example of the present embodiment, it is also possible to obtain the same effects as those of the connector 14B as the second modified example of the first embodiment.

Note that it is needless to say that the present invention is not limited to the above-described embodiments, and various changes and applications are possible without departing from the scope of the invention.

What is claimed is:

1. A medical system comprising:
    an endoscope having a shape insertable into a living body and including an image pickup portion for picking up an image of an object in the living body;
    a processor for performing signal processing on a signal when the image of the object is picked up;
    a cable whose one end side is extended from the endoscope, the cable including at the other end side thereof a connector portion connectable to a connector receiving portion of the processor;
    a light source portion including one or more LEDs for emitting light to illuminate the object and an LED substrate wherein the one or more LEDs are provided on one surface of the LED substrate, the light source portion being provided in the connector portion;
    a light transmitting portion for transmitting the light emitted from the one or more LEDs to the distal end portion to emit the light to the object;
    a first heat-radiating member including a first exposed surface exposed from an exterior of the connector portion, and provided in contact with another surface of the LED substrate;
    a second heat-radiating member including a second exposed surface exposed from the exterior, and connected to the first heat-radiating member via a heat-transfer member incorporated in the connector portion; and
    a heat-receiving portion incorporated in the processor and arranged so as to contact each of the first exposed surface and the second exposed surface when the connector portion is connected to the connector receiving portion.

2. The medical system according to claim 1, further comprising a heat-diffusing portion incorporated in the processor and capable of diffusing heat transferred to the heat-receiving portion.

* * * * *